United States Patent [19]

Ryan

[11] 4,140,701
[45] Feb. 20, 1979

[54] 2,6-METHANO-2H-1-BENZOXOCINS

[75] Inventor: Charles W. Ryan, Indianapolis, Ind.

[73] Assignee: Eli Lilly and Company, Indianapolis, Ind.

[21] Appl. No.: 831,454

[22] Filed: Sep. 8, 1977

Related U.S. Application Data

[63] Continuation-in-part of Ser. No. 702,805, Jul. 6, 1976, abandoned.

[51] Int. Cl.$^2$ .................. C07D 311/02; C07D 311/78
[52] U.S. Cl. .............................. 260/345.2; 260/345.3
[58] Field of Search ........................... 260/345.2, 345.3

[56] References Cited

U.S. PATENT DOCUMENTS

| | | | |
|---|---|---|---|
| 3,869,475 | 3/1975 | Mechonlam et al. | 260/345.2 |
| 4,054,583 | 10/1977 | Blanchard et al. | 260/345.3 |

OTHER PUBLICATIONS

Archer et al., J. Org. Chem., 42, 2277 (1977).
Razdan et al., Jacs, 96, 5860 (1974).
Razdan et al., Tetrahedron Letters, pp. 4947–4950 (1960).
Gaoni et al., Jacs, 93, 217 (1971).

*Primary Examiner*—Nicky Chan
*Attorney, Agent, or Firm*—Charles W. Ashbrook; Arthur R. Whale

[57] ABSTRACT

Novel 2-oxy-5-isopropylidene-7-hydroxy-9-substituted-2,6-methano-3,4,5,6-tetrahydro-2H-1-benzoxocins are prepared by condensing a 5-(substituted)resorcinol with a 1-alkoxy-4-(1-hydroxy-1-methylethyl)-1,4-cyclohexadiene in the presence of a suitable catalyst. The new benzoxocin derivatives are useful in the synthesis of certain dibenzo[b,d]pyran-9-ones, valuable as anti-anxiety, analgesic, and anti-depressant drugs.

17 Claims, No Drawings

2,6-METHANO-2H-1-BENZOXOCINS

CROSS REFERENCE TO RELATED APPLICATIONS

This a continuation-in-part of application Ser. No. 702,805, filed July 6, 1976, now abandoned.

BACKGROUND OF THE INVENTION

The present invention pertains to new compounds which are 2-oxy derivatives of 5-isopropylidene-7-hydroxy-9-substituted-2,6-methano-3,4,5,6-tetrahydro-2H-1-benzoxocins. Certain benzoxocin derivatives are known in the art. 2-Methyl-5-isopropenyl-7-hydroxy-9-n-pentyl-2,6-methano-3,4,5,6-tetrahydro-2H-1-benzoxocin has been prepared by reaction of boron trifluoride etherate with 2-(3-methyl- 6-isopropenyl-2-cyclohexenyl)-5-n-pentylresorcinol, commonly referred to as cannabidiol; see Gaoni and Mechoulam, Tetrahedron, 22, 1481 (1966), and J. Am. Chem. Soc., 93, 217 (1971). Razdan and Zitko reported that the above named isopropenyl benzoxocin derivative can be converted to the corresponding isopropylidene benzoxocin derivative by reaction with p-toluenesulfonic acid. These authors additionally suggested that 2-methyl-5-isopropylidene-7-hydroxy-9-n-pentyl-2,6-methano-3,4,5,6-tetrahydro-2H-1-benzoxocin can be converted to 1-hydroxy-3-n-pentyl-6,6,9-trimethyl-6$a$7,8,10$a$-tetrahydrodibenzo pyran under acidic conditions; see Tetrahedron Letters, No. 56, 4947 (1969). Recently, Razdan et al. reported the preparation of 2-methyl-5-isopropylidene-7-hydroxy-9-n-pentyl-2,6-methano-3,4,5,6-tetrahydro-2H-1-benzoxocin by reaction of 5-n-pentylresorcinol with 1-hydroxy-1-methyl-4-isopropenyl-2-cyclohexene; J. Am. Chem. Soc., 96, 5860 (1974).

All of the above-mentioned benzoxocin derivatives bear a 2-methyl substituent. Such compounds can provide, upon rearrangement, dibenzo[b,d]pyrans having a 9-methyl group. No benzoxocin derivative have hitherto been known which could be rearranged to provide a dibenzo[b,d]pyran-9-one, because the requisite benzoxocin requires an oxo substituent at the 2-position and not a methyl group, and such 2-oxo compounds have not previously been available. Certain dibenzo[b,d]pyran-9-ones preparable from 2-oxobenzoxocin derivatives are of particular importance as anti-depressant and anti-anxiety drugs, as described in U.S. Pat. Nos. 3,928,598; 3,944,673; and 3,953,603. It is therefore an object of this invention to provide 2-oxy-5-isopropylidene-7-hydroxy-9-substituted-2,6-methano-3,4,5,6-tetrahydro-2H-1-benzoxocins which can be converted to useful dibenzo[b,d]pyran-9-ones.

SUMMARY OF THE INVENTION

The present invention relates to 2-oxy derivatives of 2,6-methano-2H-1-benzoxocins. More particularly, the invention provides 2-oxy derivatives of 5-isopropylidene-7-hydroxy-9-substituted-2,6-methano-3,4,5,6-tetrahydro-2H-1-benzoxocins having the general formula

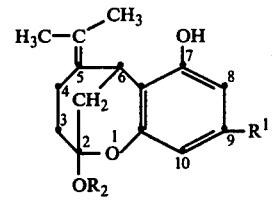

in which $R_1$ is $C_5-C_{10}$ alkyl, $C_5-C_{10}$ alkenyl, $C_5-C_8$ cycloalkyl, or $C_5-C_8$ cycloalkenyl, and $R_2$ is hydrogen or $C_1-C_4$ alkyl. Preferred benzoxocins of this invention have the above formula wherein $R_2$ is hydrogen or methyl.

DETAILED DESCRIPTION OF THE INVENTION

The 2-oxy-5-isopropylidene-7-hydroxy-9-alkyl-2,6-methano-3,4,5,6-tetrahydro-2H-1-benzoxocins of this invention, compounds having the above formula, a prepared by condensing a 5-substituted resorcinol with a 1-alkoxy-4-(1-hydroxy-1-methylethyl)-1,4-cyclohexadiene in the presence of a suitable catalyst such as boron trifluoride, boron tribromide, or zinc chloride at a temperature from about $-30°$ C. to about 30° C.

Any of a number of 5-substituted resorcinols can be utilized in the condensation, in which the 5-substituent of the resorcinol is defined by $R_1$ in the above formula. As hereinbefore noted, $R_1$ represents $C_5-C_{10}$ alkyl, $C_5-C_{10}$ alkenyl, $C_5-C_8$ Cycloalkyl, and $C_5-C_8$ cycloalkenyl. Representative examples of $C_5-C_{10}$ alkyl groups include n-pentyl, n-hexyl, 1-methylpentyl, isoheptyl, 1,1-dimethylheptyl, 1,2,3,-trimethylheptyl, isodecyl, 1-ethylheptyl, 1,1-diethylpentyl and 1,2-dimethyloctyl.

Examples of $C_5-C_{10}$ alkenyl groups include 2-pentenyl, 3-hexenyl, 1,2-dimethyl-1-heptenyl, 4-octenyl, 1,1-dimethyl-2-heptenyl, 1-ethyl-2-methyl-2-pentenyl, 1,2,3-trimethyl-3-heptenyl; and related groups.

Typical $C_5-C_8$ cycloalkyl groups include cyclopentyl, cyclohexyl, cyclohepyl and cyclooctyl. Similarly, typical $C_5-C_8$ cycloalkenyl groups include 1-cyclopentenyl, 2-cyclohexenyl, 3-cyclohexenyl, 1-cycloheptenyl, and 1-cyclooctenyl.

Examples of 5-substituted resorcinols routinely reacted with the aforementioned 1-alkoxy-4-(1-hydroxy-1-methylethyl)-1,4-cyclohexadiene to provide the 2-oxy benzoxocins of this invention include 5-n-pentylresorcinol, 5-)1,1-dimethylheptyl)resorcinol, 5-(1,2-dimethyl-1-heptenyl)resorcinol, 5-(1-ethylhexyl)resorcinol, 5-(3-hexenyl)-resorcinol, 5-cycloheptylresorcinol, 5-cyclooctylresorcinol, 5-(1-cyclohexenyl)resorcinol, 5-(2-cycloheptenyl)resorcinol, and related resorcinols.

The 1-alkoxy-4-(1-hydroxy-1-methylethyl)-1,4-cyclohexadiene reacted with a resorcinol to provide the benzoxocin of this invention has the general formula

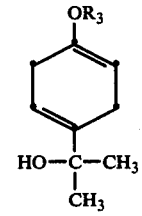

wherein $R_3$ is $C_1$-$C_4$ alkyl such as methyl, ethyl, n-propyl, isopropyl, n-butyl and isobutyl.

In accordance with this invention, approximately equimolar quantities of a 5-substituted resorcinol and a 1-alkoxy-4-(1-hydroxy-1-methylethyl)-1,4-cyclohexadiene are commingled in the presence of a suitable catalyst and in an organic solvent, at a temperature generally ranging from about −30° C. The catalysts commonly utilized in the reaction include boron tribromide, boron trifluoride, generally as the diethyl etherate complex; and zinc chloride. Preferred catalysts include boron trifluoride and zinc chloride. Stannic chloride can also be utilized as a catalyst. It should be noted that the particular catalyst utilized in the reaction, in addition to the quantity of catalyst used, as well as the precise temperature at which the reaction is conducted and the duration of reaction, determines the product obtained.

A particularly preferred catalyst is zinc chloride, since reaction of a 5-substituted resorcinol and a 1-alkoxy-4-(1-hydroxy-1-methylethyl)1,4-cyclohexadiene in the presence of zinc chloride at a temperature ranging from about 0 to about 25° C. leads to the exclusive formation of a 2,7-dihydroxy-5-isopropylidene-9-substituted-2,6-methano-3,4,5,6-tetrahydro-2H-1-benzoxocin, the benzoxocin compound of the above formula wherein $R_2$ is hydrogen. The quantity of zinc chloride used in such reaction can be an equimolar quantity, or if desired, excessive amounts ranging from about 0.5 to about 5.0 molar excess, relative to the resorcinol and cyclohexadiene reactants, can be utilized.

An additionally preferred method for preparing the benzoxocins of this invention wherein $R_2$ in the above formula is hydrogen involves the use of stannic chloride as the condensing catalyst. In particular, approximately equimolar quantities of a 5-substituted resorcinol and a 1-alkoxy-4-(1-hydroxy-1-methylethyl)-1,4-cyclohexadiene can be reacted in the presence of about a 0.1 to about a 2 molar excess of stannic chloride in a solvent such as dichloromethane. The reaction is best carried out at a temperature of about -20 to about 10° C., and the condensation to provide a 2,7-dihydroxybenzoxocin of this invention is complete as soon as the stannic chloride catalyst is added to the reaction mixture. The reaction is preferably stopped as quickly as possible, generally within 1 to 10 minutes, following the complete addition of the stannic chloride to the reaction mixture. Such quenching of the reaction is readily effected by simply adding the reaction mixture to ice, and then washing the organic solution with water. Removal of the organic solvent then provides a 2,7-dihydroxybenzoxocin of this invention in yields of about 80 to 90 percent.

It should be noted that the use of stannic chloride as the condensing catalyst requires that the reaction be permitted to continue for only a short period of time following addition of the catalyst to the reaction mixture. As is pointed out hereinbelow, prolonged contact of a 2,7-dihydroxybenzoxocin of this invention with stannic chloride effects a rearrangement of the former compound to a dl-cis-hexahydrodibenzopyranone.

When the 5-substituted resorcinol and 1-alkoxy-4-(1-hydroxy-1-methylethyl)-1,4-cyclohexadiene are condensed in the presence of about an equimolar quantity of a catalyst such as boron trifluoride at a temperature of about 25° C., the product is the corresponding 2-alkoxy-5-isopropylidene-7-hydroxy-9-substituted-2,6-methano-3,4,5,6-tetrahydro-2H-1-benzoxocin, the benzoxocin compound having the above formula wherein $R_2$ is $C_1$-$C_4$ alkyl. However, when excessive quantities of a catalyst such as boron trifluoride or boron tribromide are utilized in the reaction, for instance quantities ranging from about 0.5 to about 5.0 molar excess relative to the resorcinol and cyclohexadiene reactants, and the reaction is carried out at a temperature of from about 0° C. to about 5° C., the product is the corresponding 2,7-dihydroxy-5-isopropylidene-9-substituted-2,6-methano-3,4,5,6-tetrahydro-2H-1-benzoxocin. Surprisingly, when the condensation reaction is carried out in the presence of excessive boron trifluoride or boron trobromide, but at a temperature of about 25° C. rather than at a reduced temperature of about 0° C., the product is a dibenzopyranone derivative, specifically a dl-cis-1-hydroxy-3-subsituted-6,6-dimethyl-6,6a,7,8,10,-10α-hexahydro-9H-dibenzo[b,d]-pyran-9-one. Hence, the temperature should be kept at or below about 5° C. when such catalyst is used in the preparation of a benzoxocin of this invention.

The above-described condensation reactions to prepare benzoxocin compounds according to the above formula preferably are carried out in an organic solvent. Commonly used solvents include halogenated hydrocarbons such as dichloromethane, chloroform, 1,2-dibromoethane, 1-bromo-2-chloroethane, 1-iodopropane, 1,1-dichloroethane, 1-bromopropane, 1,1-dibromoethane, 2-chloropropane, bromobenzene, and trichloromethane; aromatic solvents such as benzene, nitrobenzene, xylene, and toluene; and ethers such as diethyl ether, dimethyl ether and methyl ethyl ether. Small amounts of water present in the reaction mixture are not detrimental to the reaction.

As noted hereinabove, while the temperature at which the reaction generally is carried out is below about 30° C., the precise temperature selected for the reaction to some extent determines the particular product formed in the reaction. At any temperature within the above-stated ranges, however, the reaction normally is substantially complete within about two to about eight hours when catalysts other than stannic chloride we utilized; however, the precise length of reaction when using such other catalysts is not critical and longer reaction time can be utilized if desired.

Upon completion of the reaction, isolation of the benzoxocin derivative which is formed normally is a simple procedure and can usually be accomplished by washing the reaction mixture with water and a dilute aqueous base, evaporating the reaction solvent, and crystallizing the residual product from common, relatively nonpolar solvents such as hexane or methyl cyclohexane.

Examples of typical benzoxocins having the above formula which can routinely be prepared and which are provided in accordance with the present invention are as follows:

2,7-dihydroxy-5-isopropylidene-9-n-pentyl-2,6-methano-3,4,5,6-tetrahydro-2H-1-benzoxocin;

2-methoxy-5-isopropylidene-7-hydroxy-9-n-decyl-2,6-methano-3,4,5,6-tetrahydro-2H-1-benzoxocin;

2-ethoxy-5-isopropylidene-7-hydroxy-9-(1,1-dimethyloctyl)-2,6-methano-3,4,5,6-tetrahydro-2H-1-benzoxocin;

2,7-dihydroxy-5-isopropylidene-9-(1,2-dimethyl-heptyl)-2,6-methano-3,4,5,6-tetrahydro-2H-1-benzoxocin;

2,7-dihydroxy-5-isopropylidene-9-(2-hexenyl)-2,6-methano-3,4,5,6-tetrahydro-2H-1-benzoxocin;

2-methoxy-5-isopropylidene-7-hydroxy-9-(1,2-dimethyl-1-heptenyl)-2,6-methano-3,4,5,6-tetrahydro-2H-1-benzoxocin;

2-isopropoxy-5-isopropylidene-7-hydroxy-9-(1-ethyl-3-pentenyl)-2,6-methano-3,4,5,6-tetrahydro-2H-1-benzoxocin;

2,7-dihydroxy-5-isopropylidene-9-(1-ethyl-2-methyl-2-butenyl)-2,6-methano-3,4,5,6-tetrahydro-2H-1-benzoxocin;

2,7-dihydroxy-5-isopropylidene-9-cyclohexyl-2,6-methano-3,4,5,6-tetrahydro-2H-1-benzoxocin;

2-n-butoxy-5-isopropylidene-7-hydroxy-9-cyclopentyl-2,6-methano-3,4,5,6-tetrahydro-2H-1-benzoxocin;

2-methoxy-5-isopropylidene-7-hydroxy-9-cycloheptyl-2,6-methano-3,4,5,6-tetrahydro-2H-1-benzoxocin;

2-ethoxy-5-isopropylidene-7-hydroxy-9-(1-cyclopentenyl)-2,6-methano-3,4,5,6-tetrahydro-2H-1-benzoxocin;

2,7-dihydroxy-5-isopropylidene-9-(1-cycloheptenyl)-2,6-methano-3,4,5,6-tetrahydro-2H-1-benzoxocin; and 2,7-dihydroxy-5-isopropylidene-9-(2-cyclooctenyl)-2,6-methano-3,4,5,6-tetrahydro-2H-benzoxocin.

The 1-alkoxy-4-(1-hydroxy-1-methylethyl)-1,4-cyclohexadienes which are required as starting materials for preparing the benzoxocin derivatives of the present invention can readily be prepared by reducing a p-alkoxy-α,α-dimethyl-benzyl alcohol. Typically, the reduction is accomplished by reaction of the benzyl alcohol derivative with a metal such as lithium in the presence of liquid ammonia and a proton source such as ethyl alcohol. Such reaction is carried out according to the standard Birch reduction conditions.

The 2-oxybenzoxocin derivatives provided by the invention are useful as intermediates in the synthesis of hexahydrodibenzopyranones. The 2-hydroxy benzoxocins, compounds having the above formula wherein $R_2$ is hydrogen, are converted, upon treatment with an aluminum halide such as aluminum chloride, to the corresponding di-trans-1-hydroxy-3-substituted-6,6-dimethyl-6,6a,7,8,10,10a-hexahydro-9H-dibenzo[b,d]-pyran-9-one. For example, reaction of a 2-hydroxy benzoxocin of this invention, such as 2,7-dihydroxy-5-isopropylidene-9-(1,2-dimethylheptyl)-2,6-methano-3,4,5,6-tetrahydro-2H-1-benzoxocin, with about a 2 to 4 molar excess of aluminum chloride in a solvent such as dichloromethane effects rearrangement to provide dl-trans-1-hydroxy-3-(1,2-dimethylheptyl)-6,6-dimethyl-6,6a,7,8,10,10a-hexahydro-9H-dibenzo[b,d]pyran-9-one. Such dl-trans-hexahydrodibenzypyranone is useful in the treatment of anxiety and depression.

Both the 2-hydroxy benzoxocins and the 2-alkoxy benzoxocins provided by this invention can be converted to the corresponding dl-cis-hexahydrodibenzopyranone by treatment with stannic chloride. For example, reaction of 2-n-propoxy-5-isopropylidene-7-hydroxy-9-n-pentyl-2,6-methano-3,4,5,6-tetrahydro-2H-1-benzoxocin with about an equimolar quantity or an excess of stannic chloride in a solvent such as benzene effects rearrangement to provide dl-cis-1-hydroxy-3-(n-pentyl)-6,6-dimethyl-6,6a,7,8,10,10a-hexahydro-9H-dibenzo[b,d]pyran-9-one. Such cis-hexahydrodibenzopyranones, while pharmacologically active in the treatment of anxiety and depression, are somewhat less active than the corresponding trans-isomer. However, treatment of such cis-hexahydrodibenzopyranones with an aluminum halide such as aluminum chloride effects epimerization to provide the corresponding pharmacologically more active trans-hexahydrodibenzopyranone. For example, reaction of dl-cis-1-hydroxy-3-(n-pentyl)-6,6-dimethyl-6,6a, 7,8,10,10a-hexahydro-9H-dibenzo[b,d]pyran-9-one with aluminum chloride in dichloromethane effects epimerization to provide the corresponding dl-trans-hexahydrodibenzopyranone.

In an effect to more fully demonstrate the operation of this invention, the following detailed examples are presented by way of illustration.

EXAMPLE 1

1-Methoxy-4-(1-hydroxy-1-methylethyl)-1,4-cyclohexadiene

A solution of 33.2 g. of p-methoxy-α,α-dimethyl-benzyl alcohol in 500 ml. of ethyl alcohol was added dropwise over a 2 hour period to a stirred solution of 14.0 g. of lithium metal shavings in 800 ml. of liquid ammonia and 200 ml. of tetrahydrofuran. Following the complete addition of the solution of the benzyl alcohol derivative, the reaction mixture was stirred from an additional fifteen minutes. Additional ethyl alcohol was then added to the reaction mixture, and the resulting solution was poured over 1000 g. of ice. The resulting aqueous mixture was extracted several times with diethyl ether. The ethereal extracts were combined, washed with saturated aqueous ammonium sulfate solution, and dried. Removal of the solvent by evaporation under reduced pressure provided the product as an oil. The oil was distilled to obtain 22 g. of 1-methoxy-4-(1-hydroxy-1-methylethyl)-1,4-cyclohexadiene. B.P. 85–90° C. at 0.3 torr nmr (CDCl$_3$): $\delta$3.55 (s, 3H, methoxy); $\delta$1.38 (s, 6H, isopropyl).

EXAMPLES 2-4

Following the procedure set forth in Example 1, the following 1-alkoxy-4-(1-hydroxy-1-methylethyl)-1,4-cyclohexadienes were prepared by reducing the corresponding p-alkoxy-α, α-dimethyl-benzylalcohol:

1-ethoxy-4-(1-hydroxy-1-methylethyl)-1,4-cyclohexadiene; B.P. 121–123° C. at 6 torr.

1-Isopropoxy-4-(1-hydroxy-1-methylethyl)-1,4-cyclohexadiene; B.P. 85–87° C. at 0.02 torr.

1-Isobutoxy-4-(1-hydroxy-1-methylethyl)-1,4-cyclohexadiene; B.P. 90–95° C. at 0.02 torr.

EXAMPLE 5

2,7-Dihydroxy-5-isopropylidene-9-(1,1-dimethylheptyl)-2,6-methano-3,4,5,6-tetrahydro-2H-1-benzoxocin A solution of 1.0 g. of 1-methoxy-4-(1-hydroxy-1-methylethyl)-1,4-cyclohexadiene in 40 ml. of dichloromethane containing 1.18 g. of 5-(1,1-dimethylheptyl) resorcinol was cooled to 5° C. in an ice-water bath and stirred while 1.5 ml. of boron trifluoride diethyl etherate was added dropwise over a five minute period. The reaction mixture was then stirred at 5° C. for five hours. The reaction mixture was next washed with a five-percent aqueous solution of sodium bicarbonate and dried. Removal of the solvent by evaporation under reduced pressure provided the product as an oil. The oil was triturated with n-hexane and then allowed to stand at room temperature for twelve hours, during which time the oil solidified. The solid product was collected by filtration and recystallized from 10 ml. of methyl cyclohexane, providing 580 mg. of 2,7-dihydroxy-5-isopropylidene-9-(1,1-dimethylheptyl)-2,6-methano-3,4,5,6-tetrahydro-2H-1-benzoxocin. M.P. 158–159° C.

Analysis calc. for $C_{24}H_{36}O_3$ Theory: C, 7.38; H, 9.74. Found: C, 77,33; H, 9.55.

nmr (CDCl$_3$): δ6.2 and 6.4 (two doublets, 2H, aromatic) δ4.3 (m, 1H, C$_6$—H)

EXAMPLE 6

2-Methoxy-5-isopropylidene-7-hydroxy-9-(1,1-dimethylheptyl)-2,6-methano-3,4,5,6-tetrahydro-2H-1-benzoxocin A solution of 2.02 g. of 1-methoxy-4-(1-hydroxy-1-methylethyl)-1,4-cyclohexadiene in 100 ml. of benzene containing 2.36 g. of 5-(1,1-dimethylheptyl)resorcinol was stirred at 25° C. while 1 ml. of boron trifluoride diethyl etherate was added in one portion. The reaction mixture was stirred for five hours at 25° C., and was then washed with water and with a five-percent aqueous solution of sodium bicarbonate. After drying the organic solution, the solvent was removed by evaporation under reduced pressure to provide 4.4 g. of an oil. After standing for several hours at 25° C., the oil solidified. The solid product so formed was washed with n-hexane and then recrystallized from cyclohexane, providing 1.55 g. of 2-methoxy-5-isopropylidene-7-hydroxy-9-(1,1-dimethylheptyl)-2,6-methano-3,4,5,6-tetrahydro-2H-1-benzoxocin. M.P. 131–133° C. Mass spectal analysis: molecular ion at m/e 386.

EXAMPLE 7

2,7-Dihydroxy-5-isopropylidene-9-(1,1-dimethylheptyl)-2,6-methano-3,4,5,6-tetrahydro-2H-1-benzoxocin A solution of 2.0 g. of 1-methoxy-4-(1-hydroxy-1-methylethyl)-1,4-cyclohexadiene in 80 ml. of commercial grade dichloromethane and 2.36 g. of 5-(1,1-dimethylheptyl)resorcinal was cooled to about 5° C. In an ice-water bath and stirred while 3.4g. of zinc chloride was added in one portion. The reaction mixture was stirred for four hours at a temperature ranging from about 0 to 5° C. The reaction mixture then was washed with water and with dilute aqueous sodium hydroxide solution. After drying the reaction mixture, the solvent was removed by evaporation under reduced pressure to provide the product as an oil. The oil soldified upon standing at room temperature, and was triturated with n-hexane to provide 1.8 g. of 2,7-dihydroxy-5-isopropylidene-9-(1,1-dimethylheptyl)-2,6-methano-3,4,5,6-tetrahydro-2H-1-benzoxocin. M.P. 153–155° C.

EXAMPLE 8

2,7-Dihydroxy-5-isopropylidene-9-(1,1-dimethylheptyl)-2,6-methano-3,4,5,6-tetrahydro-2H-1-benzoxocin A solution of 2.52 g. of 1-isobutoxy-4-(1-hydroxy-1-methylethyl)-1,4-cyclohexadiene, 2.36 g. of 5-(1,1-dimethylheptyl) resorcinol and 3.4 g. of zinc chloride in 50 ml. of dichloromethane was treated according to the procedure of Example 7. Normal workup afforded 1.6 g. of 2,7-dihydroxy-5-isopropylidene-9-(1,1-dimethylheptyl)-2,6-methano-3,4,5,6-tetrahydro-2H-1-benzoxocin, which was shown by thin layer chromatography and NMR to be identical to the product of Example 7.

EXAMPLE 9

2-Ethoxy-5-isopropylidene-7-hydroxy-9-(1,1-dimethylheptyl)-2,6-methano-3,4,5,6-tetrahydro-2H-1-benzoxocin A solution of 2.36 g. of 5-(1,1-dimethylheptyl)-resorcinol and 2.2 g. of 1-ethoxy-4-(1-hydroxy-1-methylethyl)-1,4-cyclohexadiene in 100 ml. of benzene was stirred at 25° C. while 1 ml. of boron trifluoride diethyl etherate was added in one portion. The reaction mixture was then stirred for an additional five hours, and then washed with water, twice with 1N sodium hydroxide and again with water. The organic solution was dried and the solvent was removed by evaporation under reduced pressure to provide 2.91 g. of the product as an oil. The oil was purified by preparative thick layer chromatography, eluting with a 4 to 1 solution of toluene in ethyl acetate. The appropriate bond was collected and the product washed therefrom with acetone. Evaporation of the acetone provided 2-ethoxy-5-isopropylidene-7-hydroxy-9-(1,1-dimethylheptyl)-2,6-methano-3,4,5,6-tetrahydro-2H-1-benzoxocin, which was then recrystallized from ethyl alcohol. Mass spectral analysis: m/e theory 400; found 400.

EXAMPLE 10

2-Isopropoxy-5-isopropylidene-7-hydroxy-9-(1,1-dimethylheptyl)-2,6-methano-3,4,5,6-tetrahydro-2H-1-benzoxocin A solution of 2.36 g. 5-(1,1-dimethylheptyl)-resorcinol and 2.35 g. of 1-isopropoxy-4-(1-hydroxy-1-methylethyl)-1,4-cyclohexadiene in 100 ml. of benzene containing 1 ml. of boron trifluoride diethyl etherate was stirred at about 25° C. for seven hours. The reaction mixture was then washed with water, twice with 1N sodium hydroxide solution, again with water, and dried. Removal of the solvent by evaporation under reduced pressure afforded 3.24 g. of an oil. Thin layer chromatography demonstrated that the oil consisted of the desired 2-isopropoxy-5-isopropylidene-7-hydroxy-9-(1,1-dimethylheptyl)-2,6-methano-3,4,5,6-tetrahydro-2H-1-benzoxocin in addition to 2,7-dihydroxy-5-isopropylidene-9-(1,1-dimethylheptyl)-2,6-methano-3,4,5,6-tetrahydro-2H-1-benzoxocin.

EXAMPLE 11

2-Isobutoxy-5-isopropylidene-7-hydroxy-9-(1,1-dimethylheptyl)-2,6-methano-3,4,5,6-tetrahydro-2H-1-benzoxocin A solution of 2.52 g. of 1-isobutoxy-4-(1-hydroxy-1-methylethyl)-1,4-cyclohexadiene, 2.36 g. of 5-(1,1-dimethylheptyl)resorcinol, and 1 ml. of boron trifluoride diethyl etherate in 100 ml. of benzene was stirred at 24° C. for seven hours. The reaction mixture then was washed with water, twice with 1N sodium hydroxide and again with water. The solution was dried and the solvent was removed by evaporation under reduced pressure to provide 3.64 g. of an oil which was shown by thin layer chromatography to consist of 2-isobutoxy-5-isopropylidene-7-hydroxy-9-(1,1-dimethylheptyl)-2,6-methano-3,4,5,6-tetrahydro-2H-1-benzoxocin, the corresponding 2,7-dihydro benzoxocin, and a small amount of dl-cis-1-hydroxy-3-(1,1-dimethylheptyl)-6,6-dimethyl-6,6a,7,8,10,10a-hexahydro-9H-dibenzo-[b,d]pyran-9-one.

EXAMPLE 12

2,7-Dihydroxy-5-isopropylidene-9-(1,1-dimethylheptyl)-2,6-methano-3,4,5,6-tetrahydro-2H-1-benzoxocin A solution of 11.8 g. of 5-(1,1-dimethylheptyl)-resorcinol, 12.0 g. of 1-methoxy-4-(1-hydroxy-1-methylethyl)-1,4-cyclohexadiene and 0.9 ml. of water in 100 ml. of dichloromethane stabilized with cyclohexane (ie. commercial grade dichloromethane) was stirred and cooled to −20° C. in a dry ice-acetone bath. To the cold stirred solution was added 13 ml. of stannic chloride dropwise at a rapid rate over three minutes, during which time the temperature of the reaction mixture increased to −11° C. Immmediately following complete addition of the stannic chloride to the reaction mixture, the mixture was poured into 200 g. of ice, and 50 ml. of water was added to the ice mixture. The organic layer was separated, washed twice with 200 ml. portions of 1N sodium hydroxide and then with 250 ml. of water. The organic layer next was dried, and the solvent was removed by evaporation under reduced pressure to provide 20.5 g. of the product as a solid. The solid thus formed was recrystallized from n-hexane to afford 16.2 g. (87 percent yield) of 2,7-dihydroxy-5-isopropylidene-9-(1,1-dimethylheptyl)-2,6-methano-3,4,5,6-tetrahydro-2H-1-benzoxocin. M.P. 148–152° C.

EXAMPLE 13 dl-trans-1-hydroxy-3-(1,1-dimethylheptyl)-6,6-dimethyl-6,6a,7,8,10,10a-hexahydro-9H-dibenzo[b,d]pyran-9-one A solution of 100 mg. of 2,7-dihydroxy-5-isopropylidene-9-(1,1-dimethylheptyl)-2,6-methano -3,4,5,6-tetrahydro-2H-1-benzoxocin in 5 ml. of dichloromethane was stirred at about 24° C. while 100 mg. of aluminum chloride was added in one portion. The reaction mixture was stirred at 24° C. for six hours, and was then washed with 1N hydrochloric acid solution, with water, and dried. Removal of the solvent by evaporation under reduced pressure provided a solid residue, which was recrystallized from hexane to provide dl-trans-1-hydroxy-3-(1,1-dmethylheptyl)-6,6-dimethyl-6,6a,7,8,10,10a-hexahydro-9H-dibenzo[b,d]pyran-9-one. M.P. 160–161° C.

I claim:

1. A compound of the formula

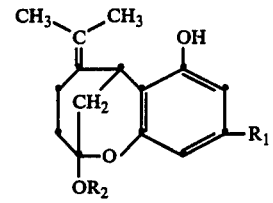

wherein:

$R_1$ is $C_5$–$C_{10}$ alkyl, $C_5$–$C_{10}$ alkenyl, $C_5$–$C_8$ cycloalkyl, or $C_5$–$C_8$ cycloalkenyl; and $R_2$ is hydrogen or $C_1$–$C_4$ alkyl.

2. The compound of claim 1 wherein $R_1$ is $C_5$–$C_{10}$ alkyl.

3. The compound of claim 2 wherein $R_2$ is hydrogen.

4. The compound according to claim 3, said compound being 2,7-dihydroxy-5-isopropylidene-9-(1,1-dimethylheptyl)-2,6-methano-3,4,5,6-tetrahydro-2H-1-benzoxocin.

5. The compound according to claim 3, said compound being 2,7-dihydroxy-5-isopropylidene-9-(1,2-dimethylheptyl)-2,6-methano-3,4,5,6-tetrahydro-2H-1-benzoxocin.

6. The compound according to claim 3, said compound being 2,7-dihydroxy-5-isopropylidene-9-(n-pentyl)-2,6-methano-3,4,5,6-tetrahydro-2H-1-benzoxocin.

7. The compound according to claim 3, said compound being 2,7-dihydroxy-5-isopropylidene-9-(n-decyl)-2,6-methano-3,4,5,6-tetrahydro-2H-1-benzoxocin.

8. The compound according to claim 3, said compound being 2,7-dihydroxy-5-isopropylidene-9-(n-heptyl)-2,6-methano-3,4,5,6-tetrahydro-2H-1-benzoxocin.

9. The compound according to claim 3, said compound being 2,7-dihydroxy-5-isopropylidene-9-(1-methylheptyl)-2,6--methano-3,4,5,6--tetrahydro-2H-1-benzoxocin.

10. The compound of claim 2 wherein $R_2$ is $C_1$–$C_4$ alkyl.

11. The compound of claim 10 wherein $R_2$ is methyl.

12. The compound according to claim 11, said compound being 2-methoxy-5-isopropylidene-7-hydroxy-9-(1,1-dimethylheptyl)-2,6-methano-3,4,5,6-tetrahydro-2H-1-benzoxocin.

13. The compound of claim 11, said compound being 2-methoxy-5-isopropylidene-7-hydroxy-9-(1,2-dimethylheptyl)-2,6-methano-3,4,5,6-tetrahydro-2H-1-benzoxocin.

14. The compound of claim 10 wherein $R_2$ is ethyl.

15. The compound according to claim 14, said compound being 2-ethoxy-5-isopropylidene-7-hydroxy-9-(1,1-dimethylheptyl)-2,6-methano-3,4,5,6-tetrahydro-2H-1-benzoxocin.

16. The compound of claim 10 wherein $R_2$ is isopropyl.

17. The compound of claim 10 wherein $R_2$ is isobutyl.